(12) United States Patent
Iwata

(10) Patent No.: US 8,217,364 B2
(45) Date of Patent: Jul. 10, 2012

(54) PARTICLE BEAM IRRADIATION APPARATUS

(75) Inventor: Takaaki Iwata, Chiyoda-ku (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 94 days.

(21) Appl. No.: 12/989,767

(22) PCT Filed: Jun. 9, 2009

(86) PCT No.: PCT/JP2009/060530
§ 371 (c)(1),
(2), (4) Date: Oct. 26, 2010

(87) PCT Pub. No.: WO2010/143266
PCT Pub. Date: Dec. 16, 2010

(65) Prior Publication Data
US 2011/0174994 A1 Jul. 21, 2011

(51) Int. Cl.
*G21K 5/04* (2006.01)
(52) U.S. Cl. .................. 250/396 R; 250/492.3
(58) Field of Classification Search .............. 250/396 R, 250/396 ML, 492.3
See application file for complete search history.

(56) References Cited

U.S. PATENT DOCUMENTS

| | | | |
|---|---|---|---|
| 6,034,377 A | 3/2000 | Pu | |
| 7,560,715 B2 | 7/2009 | Pedroni | |
| 2008/0006776 A1 | 1/2008 | Furukawa et al. | |
| 2009/0039256 A1 | 2/2009 | Fujii et al. | |
| 2011/0121195 A1* | 5/2011 | Harada et al. | 250/396 ML |
| 2011/0147604 A1* | 6/2011 | Iwata | 250/396 ML |

FOREIGN PATENT DOCUMENTS

| | | |
|---|---|---|
| JP | 11-142600 A | 5/1999 |
| JP | 2002-141199 A | 5/2002 |
| JP | 2005-296162 A | 10/2005 |
| JP | 2006-166947 A | 6/2006 |
| JP | 2007-132902 A | 5/2007 |
| JP | 2007-534391 A | 11/2007 |
| JP | 2009-000347 A | 1/2009 |
| WO | WO 01/69643 A1 | 9/2001 |
| WO | WO 2005/102453 | 11/2005 |
| WO | WO 2007/029520 | 3/2007 |

OTHER PUBLICATIONS

T. Iwata, U.S. Appl. No. 12/991,231, entitle "Particle Bean Irradiation Apparatus" filed on Nov. 5, 2010. Kanai et al., "Spot scanning system for proton radiotherapy", Med. Phys., Jul./Aug. 1980, pp. 365-369, vol. 7, No. 4.
Ogawa et al., "Absorption Equivalent Thickness (AET) Method and Pencil Beam Method for Electron Beam Treatment Planning", Japanese J. Radiol. Technol., Sep. 9, 1986, pp. 628-634, vol. 42, No. 5 (English Summary included).

* cited by examiner

*Primary Examiner* — Kiet T Nguyen
(74) *Attorney, Agent, or Firm* — Buchanan Ingersoll & Rooney PC

(57) ABSTRACT

A particle beam irradiation apparatus which can perform high-precision beam irradiation position is obtained. The apparatus is provided with inverse mapping means having an inverse mapping mathematical expression model for generating an command value for the scanning electromagnet and an command value for kinetic energy of the charged particle beam from a desired irradiation position coordinate of the charged particle beam in an irradiation subject so that irradiation to the irradiation subject is implemented on the basis of the command values concerned, and the scanning electromagnet and the kinetic energy of the charged particle beam are controlled on the basis of the command values generated from the desired irradiation position coordinate of the charged particle beam in the irradiation subject by using the inverse mapping mathematical expression model, thereby irradiating the irradiation subject with the charged particle beam while scanning the charged particle beam.

9 Claims, 8 Drawing Sheets

3a: X-DIRECTION SCANNING ELECTROMAGNET
3b: Y-DIRECTION SCANNING ELECTROMAGNET
12: FIRST BEAM PROFILE MONITOR
13: SECOND BEAM PROFILE MONITOR
14: WATER PHANTOM

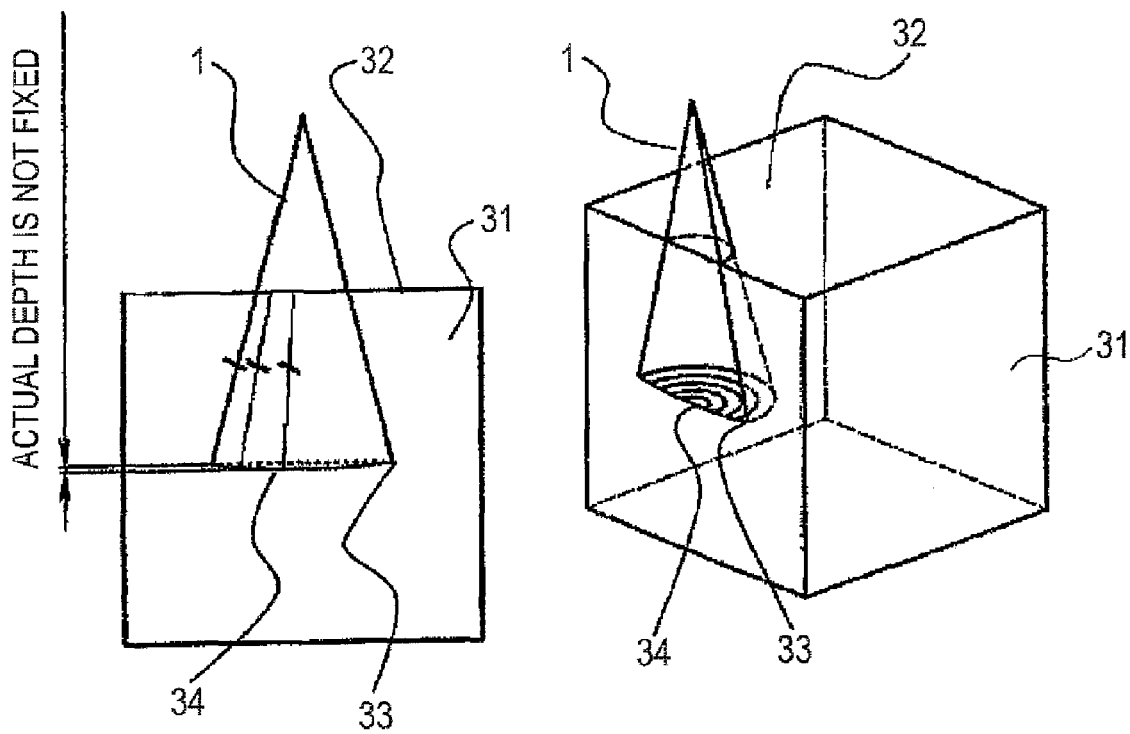

PARTICLE BEAM IRRADIATION APPARATUS

TECHNICAL FIELD

The present invention relates to a particle beam irradiation apparatus used for medical care such as a cancer treatment, etc. and for researches, and particularly to a particle beam irradiation apparatus for performing scanning irradiation such as spot-scanning, raster-scanning or the like.

BACKGROUND ART

Abroad irradiation method is an irradiation method which has been most broadly used in a particle beam irradiation apparatus used for medical care such as a cancer treatment, etc. and for researches. The broad irradiation method is a method of spreading a charged particle beam by using a scattering member and a wobbler electromagnet and reducing irradiation to places other than a diseased site by using a collimator or a bolus.

In addition to the broad irradiation method for irradiating an irradiation subject area at a stroke, a scanning irradiation method for irradiating a diseased site as an irradiation subject with a charged particle beam every small area while scanning the charged particle beam, such as spot scanning or raster scanning has been proposed (for example, non-patent document 1). There have been also proposed a technique in which a conventional particle beam irradiation apparatus for performing scanning irradiation disclosed in the non-patent document 1 is further modified so that a scanning electromagnet is disposed at the upstream side of a final bending electromagnet, thereby remarkably reducing the radius of a gantry (patent document 1) and a technique in which the scanning electromagnet can be omitted (patent document 2). Furthermore, means for correcting a deflection scanning position displacement in a charged particle bean scanning apparatus used to irradiate a beam onto a sample has been proposed although it is not a particle beam irradiation apparatus for medical care or for researches (patent document 3).

It is general in the scanning irradiation method that a part for preventing irradiation to normal tissues other than a diseased site such as a collimator or a bolus used in the broad irradiation method is not provided, and thus higher beam position precision than the broad irradiation method is required. As described above, a device for compensating the beam position precision has been hardly disclosed although the scanning irradiation method requires the higher beam position precision than the broad irradiation method.

Furthermore, when a charged particle beam of proton, carbon ion or the like is incident into substance such as the body or the like, it travels till the specific depth (called as a range) corresponding to the energy of the charged particle beam in the substance, a peak at which the maximum energy is applied from the charged particle beam to the substance exists in the neighborhood of the terminal of the range (called as "Bragg peak"), and the charged particle beam has a characteristic that the Bragg peak thereof has a shaper depth dose distribution as compared with other radiation rays such as X-ray, etc. The particle beam irradiation apparatus suppresses the charged particle beam from affecting normal tissues by utilizing this characteristic, whereby the dose is concentrically irradiated onto the diseased site. From this viewpoint, in a scanning particle beam irradiation apparatus or treatment plan apparatus for performing spot scanning or raster scanning, control amounts for scanning means and an accelerator have been hitherto calculated on the assumption that the in-body depth direction (Z direction) of the desired irradiation position and the X-direction and Y-direction perpendicular to the Z direction can be separately controlled by adjusting the energy of the charged particle beam and controlling the scanning means such as the scanning electromagnet or the like, respectively.

PRIOR ART DOCUMENT

Patent Document

Patent Document 1: JP-A-2007-534391
Patent Document 2: JP-A-2006-166947
Patent Document 3: Pamphlet of Internal Publication No. WO01/69643

Non-Patent Document

Non-patent Document 1: Tatsuaki Kanai, et al., "Spot scanning system for proton radiotherapy", Medical Physics, July./August 1980, Vol. 7, No. 4, pp 365-369

SUMMARY OF THE INVENTION

Problem to be Solved by the Invention

When the charged particle beam is a parallel beam having a fixed traveling direction, the z coordinate of the beam irradiation position can be uniquely determined by only the energy of the charged particle beam. However, in a particle beam irradiation apparatus in which the direction of the beam is controlled by scanning means such as an actual scanning electromagnet or the like, the charged particle beam becomes a fan beam (one-dimensional scanning) which spreads out in a fan-like form or a cone beam (two-dimensional scanning) which spreads out in a conical shape. Therefore, the z coordinate of the beam irradiation position cannot be uniquely determined by the energy of the charged particle beam. The effect of the fan beam on the irradiation position is called as an fan beam effect, and the effect of the cone beam on the irradiation position is called as a cone beam effect.

FIGS. 8A and 8B are diagrams showing the fan beam effect and the cone beam effect. In FIGS. 8A and 8B, 1 represents a charged particle beam, 31 represents the body of a patient, and 32 represents the surface of the body. FIG. 8A shows the fan beam effect, and when the charged particle beam 1 is one-dimensionally scanned, the z-coordinate of the end portion 33 of the irradiation position and the z-coordinate of the center portion 34 are not fixed. FIG. 8B shows the cone beam effect, and when the charged particle beam 1 is two-dimensionally scanned, the z-coordinate of the end portion 33 of the irradiation position and the z-coordinate of the center portion 34 are not fixed.

The present invention has been implemented to solve the foregoing problem, and has an object to provide a particle beam irradiation apparatus that can implement a high-precision beam irradiation position.

Means of Solving the Problem

According to the particle beam irradiation apparatus for irradiating an irradiation subject with a charged particle beam from the accelerator by controlling the accelerator and the scanning electromagnet by the controller, the scanning electromagnet has an X-direction scanning electromagnet and a Y-direction scanning electromagnet for scanning in a direction perpendicular to a scanning direction of the X-direction scanning electromagnet, the controller has X-direction, Y-direction and kinetic energy inverse mapping mathematical expression models for generating an X-direction command value for exciting the X-direction scanning electromagnet, a Y-direction command value for exciting the Y-direction scanning electromagnet and an command value of kinetic energy for the accelerator from a desired irradiation position coordinate of the charged particle beam in the irradiation subject so that irradiation to the irradiation subject is implemented on the basis of the command values concerned, each of the X-direction, Y-direction and kinetic energy inverse mapping mathematical expression models contain all of three variables when the desired irradiation position coordinate is represented by the three variables concerned, and the X-direction and Y-direction scanning electromagnets and the accelerator are controlled on the basis of the X-direction, Y-direction and kinetic energy command values generated from the desired irradiation position coordinate of the charged particle beam in the irradiation subject by the X-direction, Y-direction and kinetic energy inverse mapping mathematical expression models, thereby irradiating the irradiation subject with the charged particle beam.

Furthermore, in the particle beam irradiation apparatus of this invention, the unknown coefficients existing in each of the X-direction, Y-direction and kinetic energy inverse mapping mathematical expression models as the polynomial expressions are determined by inputting plural pairs of command values preset for the X-direction and Y-direction scanning electromagnets and also inputting plural kinetic energy command values preset to the accelerator to control the charged particle beam, and applying a least square method or a weighted least square method to actual data of actually irradiated irradiation position coordinates.

Effect of the Invention

According to the particle beam irradiation apparatus of the present invention, the controller has X-direction, Y-direction and kinetic energy inverse mapping mathematical expression models for generating an X-direction command value for exciting the X-direction scanning electromagnet, a Y-direction command value for exciting the Y-direction scanning electromagnet and an command value of kinetic energy for the accelerator for accelerating charged particle beam from a desired irradiation position coordinate of the charged particle beam in the irradiation subject so that irradiation to the irradiation subject is implemented on the basis of the command values concerned, and each of the X-direction, Y-direction and kinetic energy inverse mapping mathematical expression models contain all of three variables when the desired irradiation position coordinate is represented by the three variables concerned. Therefore, there can be obtained the particle beam irradiation apparatus which can implement high-precision beam irradiation position. Furthermore, there can be implemented the high-precision beam irradiation position considering the variation of the irradiation position coordinate which is dependent on the fan beam effect and the cone beam effect.

Furthermore, according to the particle beam irradiation apparatus of the present invention, the unknown coefficients existing in each of the X-direction, Y-direction and kinetic energy inverse mapping mathematical expression models as the polynomial expressions are determined by inputting plural pairs of X-direction and Y-direction command values preset for the X-direction and Y-direction scanning electromagnets and also inputting plural preset kinetic energy command values to the accelerator to control the charged particle beam, and applying a least square method or a weighted least square method to actual data of actually irradiated irradiation position coordinates. Accordingly, the unknown coefficients are based on the actual data, and thus there can be obtained the particle beam irradiation apparatus which can implement high-precision beam irradiation position. Accordingly, there can be implemented the high-precision beam irradiation position considering the variation of the irradiation position coordinate which is dependent on the fan beam effect and the cone beam effect.

BRIEF DESCRIPTION OF DRAWINGS

FIGS. 8A and 8B are diagrams showing a fan beam effect and a cone beam effect.

BEST MODES FOR CARRYING THE INVENTION

Basic Technique of Invention

Figure 1:
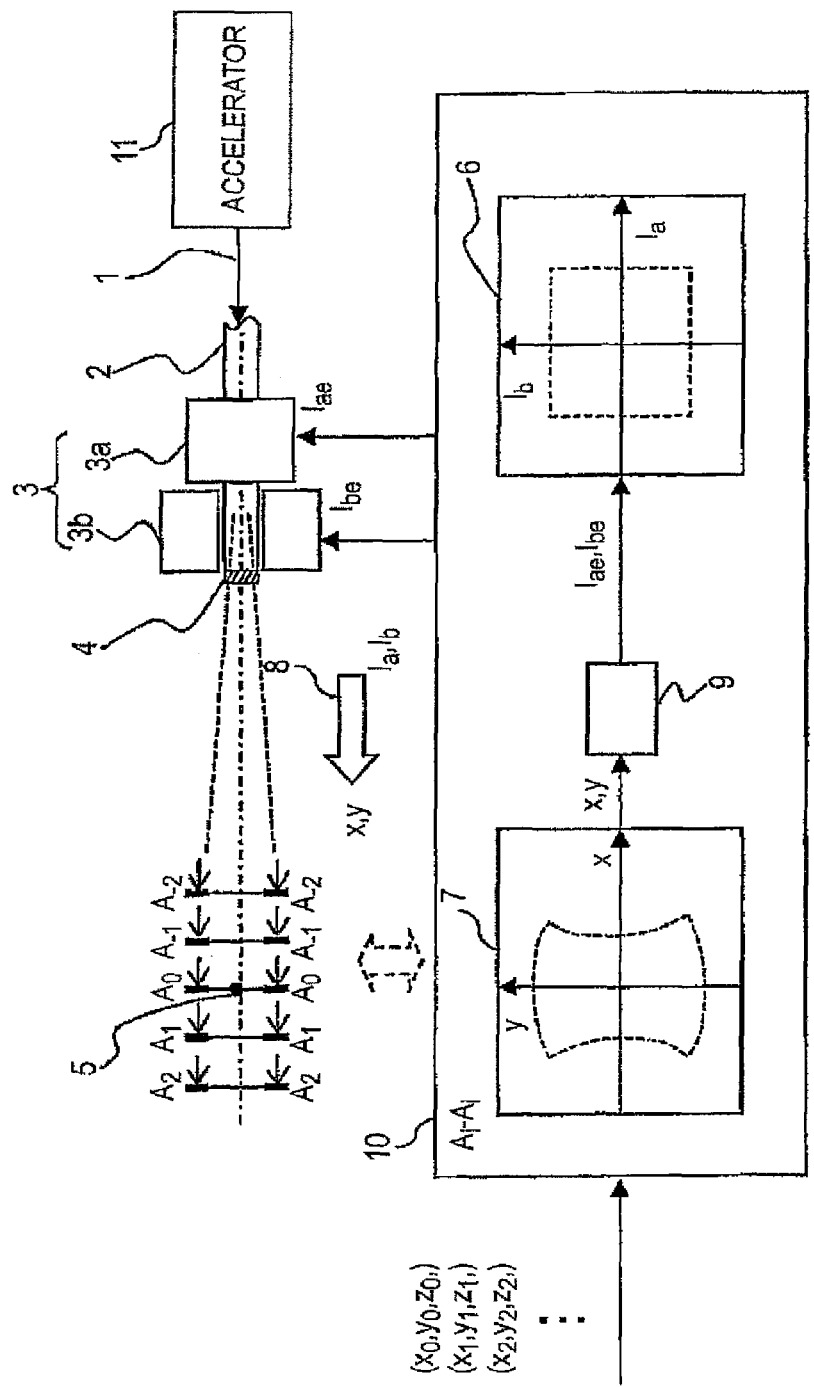
FIG. 1 is a diagram showing the construction of a particle beam irradiation apparatus according to a basic technique of the present invention.

FIG. 1 is a diagram showing the configuration of a particle beam irradiation apparatus for performing scanning irradiation according to a basic technique of the present invention. The particle beam irradiation apparatus has an accelerator 11 for accelerating a charged particle beam 1 to obtain a charged particle beam 1 having desired kinetic energy, a beam transport duct 2 for transporting the charged particle beam 1, a scanning electromagnet (scanning electromagnet) 3 for scanning the charged particle beam 1, a beam outlet window 4 for picking up a beam, a scanning controller 10 for transmitting an command value to the scanning electromagnet 3, etc. A beam transport system having the beam transport duct 2 is provided with a bending electromagnet, a beam monitor, a shielding electromagnet, a beam damper, an irradiation path bending electromagnet, etc. In the particle beam irradiation apparatus according to the basic technique of the invention, the scanning controller 10 has an inverse mapping mathematical expression model for a mapping from a beam irradiation position coordinate space 7 to a scanning electromagnet command value space 6. In other words, the scanning controller 10 has inverse mapping means 9 for generating, for a desired beam irradiation position coordinate, an estimation value of an command value for the scanning electromagnet 3 to implement the desired beam irradiation position coordinate concerned.

Next, the operation of the particle beam irradiation apparatus will be described. The charged particle beam 1 which has been accelerated to have a desired kinetic energy by the accelerator 11 is passed through the beam transport duct 2 and led to an irradiation unit. The charged particle beam 1 is further picked up through the beam outlet window 4, and irradiated to an isocenter 5 as an irradiation reference point. In general, in order to selectively scan and irradiate a diseased site as an irradiation subject, the X and Y directions of the beam irradiation position of the charged particle beam 1 are generally controlled by an X-direction scanning electromagnet (X-direction scanning electromagnet) 3a and a Y-direction scanning electromagnet (Y-direction scanning electromagnet) 3b provided to the outside of the beam transport duct 2, and also the kinetic energy of the charged particle beam 1 is varied by the accelerator 11, whereby the Z-direction of the beam irradiation position (the depth direction of the diseased site) is controlled. The beam irradiation position is controlled according to a method of executing central control with an irradiation control device 23 (see FIG. 5) for controlling the overall particle beam irradiation apparatus or a method of executing distributed control with the scanning controller 10 for controlling the scanning electromagnet and the kinetic energy of the charged particle beam 1 of the accelerator.

In the basic technique, the scanning controller 10 for controlling the irradiation position of the charged particle beam 1 is provided with the inverse mapping means 9 having the inverse mapping mathematical expression model for the mapping from the beam irradiation position coordinate space 7 to the scanning electromagnet command value space 6. A preferable example of the inverse mapping mathematical expression model is a polynomial expression model including desired irradiation position coordinates. A polynomial expression for the maximum order=2 is represented by the following mathematical expression 1. In the basic technique, the Z-direction (depth direction) of the beam irradiation position is assumed to be uniquely determined by the kinetic energy of the charged particle beam, and plural inverse mapping mathematical expression models are created for different kinetic energies.

[mathematical expression 1]

mathematical expression 1

$$\begin{cases} I_{ae} = a_{00} + a_{01}x + a_{02}x^2 + a_{10}y + a_{11}xy + a_{20}y^2 \\ I_{be} = b_{00} + b_{01}x + b_{02}x^2 + b_{10}y + b_{11}xy + b_{20}y^2 \end{cases}$$

Here, $a_{00}, a_{01}, a_{02}, \ldots, b_{00}, b_{01}, b_{02}, \ldots$ represent coefficients (unknown parameters) for determining the characteristic of the inverse mapping mathematical expression model. $I_{ae}$ and $I_{be}$ represent estimation values of the respective command values for the X, Y-direction scanning electromagnets when the irradiation position coordinate of the charged particle beam is represented by (x,y). The coefficients (unknown parameters) for determining the characteristic of the inverse mapping mathematical expression model may be determined by performing test irradiation for calibration in advance and applying a least square method or the like on the actual data of the test irradiation.

Figure 2:
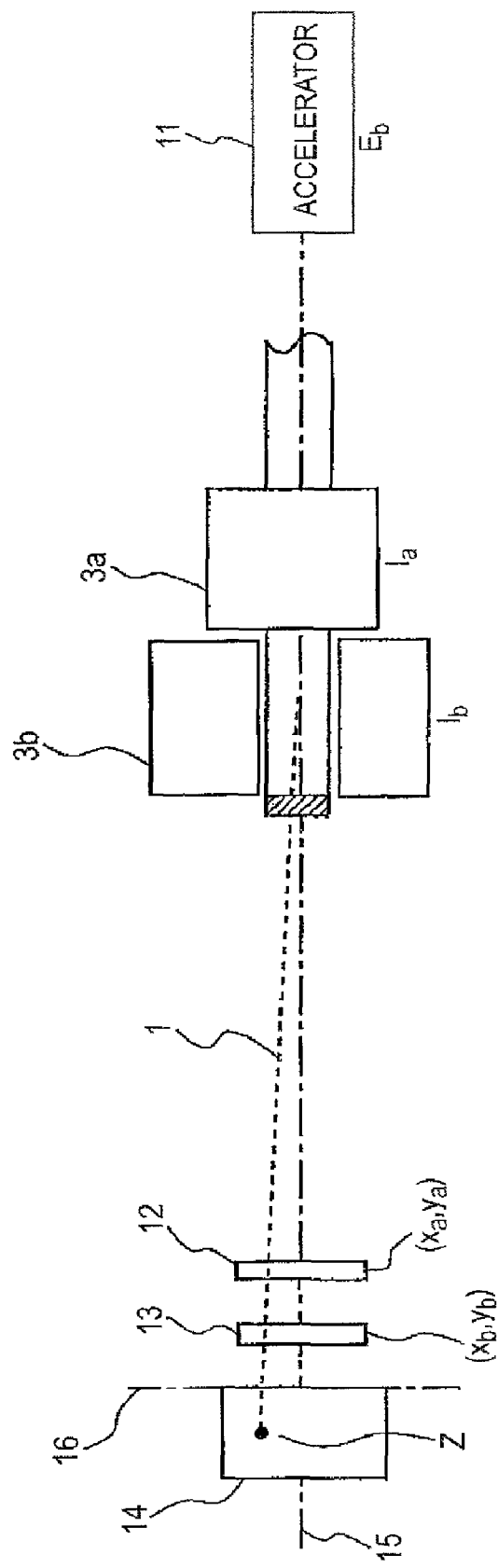
FIG. 2 is a diagram showing a method of calculating coefficients (unknown parameters) from actual data at the calibration time in the present invention.
Figure 3:
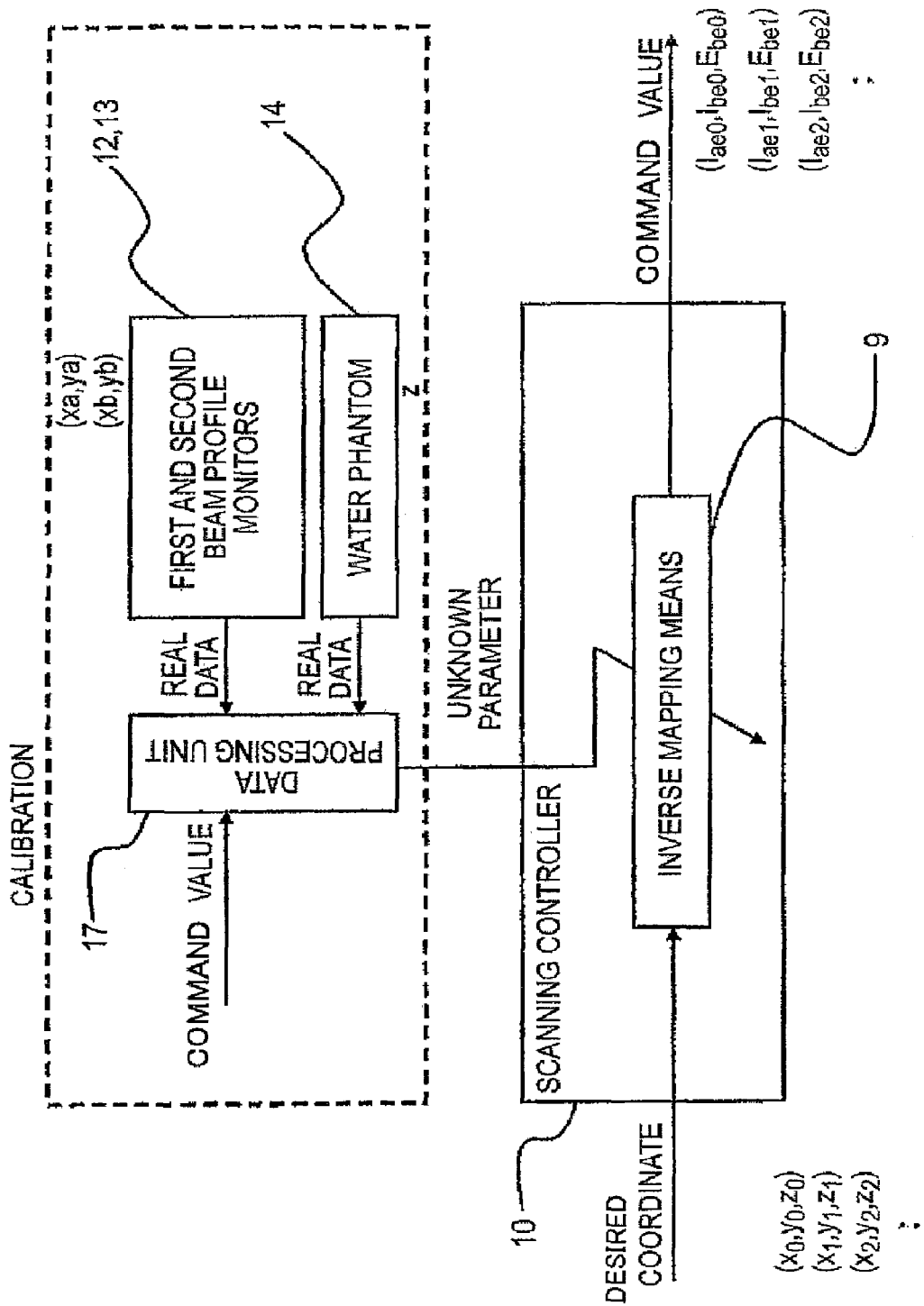
FIG. 3 is a block diagram showing the method of calculating the coefficients (unknown parameters) in the present invention.
Figure 4:
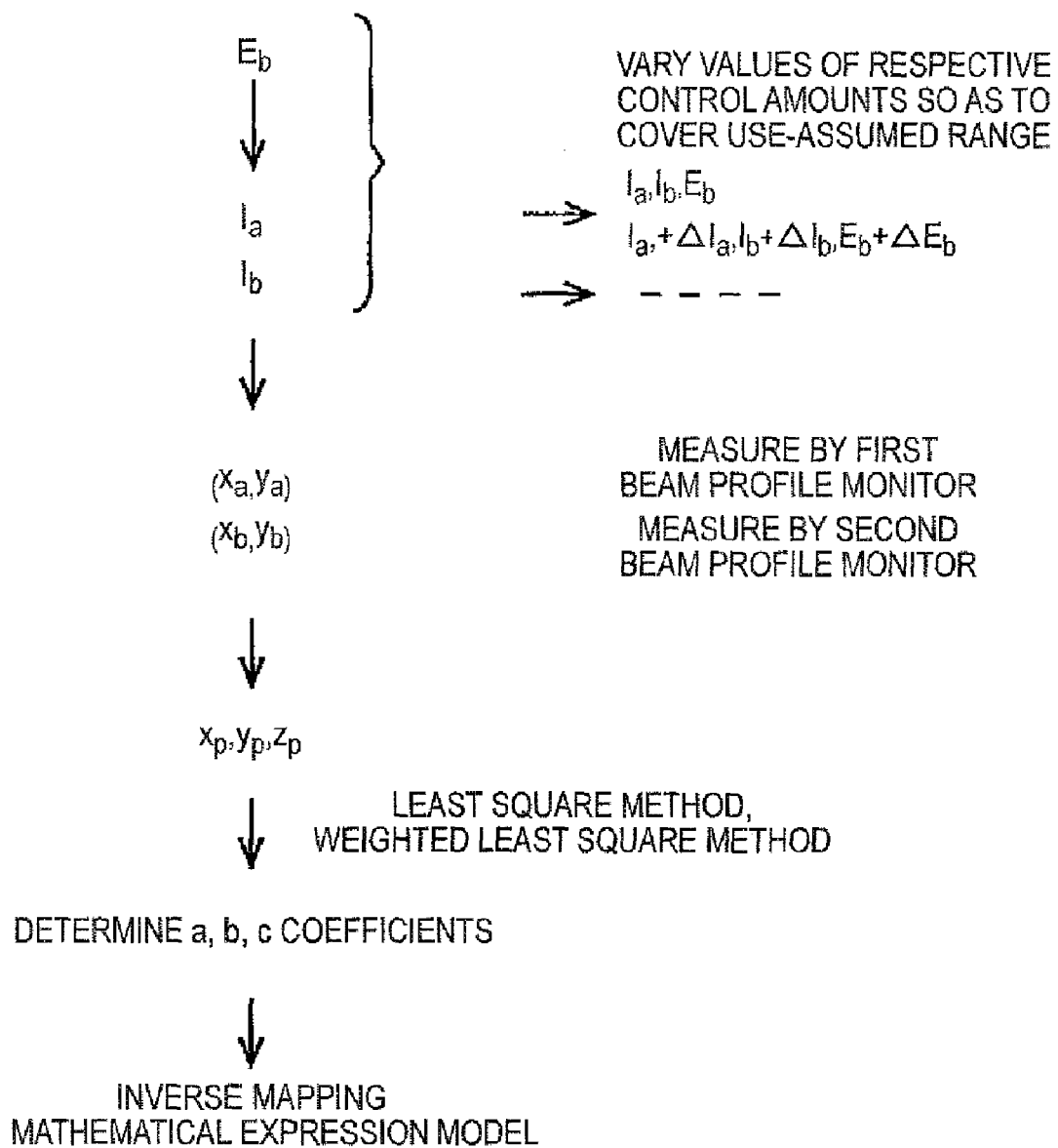
FIG. 4 is a flowchart showing the method of calculating the coefficients (unknown parameters) in this invention.

FIG. 2 is a diagram showing a method of calculating the coefficients (unknown parameters) from the actual data obtained under the calibration. In FIG. 1, 8 represents the direction of a forward mapping (actual physical phenomenon). FIG. 3 is a block diagram showing the method of calculating the coefficients (unknown parameters). FIG. 4 is a flowchart showing the method of calculating the coefficients (unknown parameters). In each figure, the same reference numerals represent same or corresponding parts. In the figures, 12 represent a first beam profile monitor, and it is disposed vertically to a reference irradiation axis 15 of the charged particle beam, and outputs the two-dimensional passage position coordinate ($x_a$, $y_a$) of the charged particle beam to be irradiated. 13 represents a second beam profile monitor, and it is disposed vertically to the reference irradiation axis 15 of the charged particle beam so as to be spaced from the first beam profile monitor 12 at a predetermined interval, and outputs the two-dimensional passage position coordinate ($x_b$, $y_b$) of the charged particle beam to be irradiated. 14 represents a water phantom, and it is disposed vertically to the reference irradiation axis 15 so that the surface thereof is fit to the body surface 16 of a patient, and outputs the coordinate $z_p$ in the depth direction of the position coordinate which the charged particle beam to be irradiated reaches. The first and second beam profile monitors 12 and 13 and the water phantom 14 are arranged when the unknown parameters are calculated or the charged particle beam is corrected or checked, and moved when the patient is irradiated with the charged particle beam.

The test irradiation for calibration is executed while the following values are fluctuated by the scanning controller 10.

Command value $I_a$ for the X-direction scanning electromagnet (=current value, current value calculated and corrected in consideration of hysteresis, set magnetic field intensity, etc.)

Command value $I_b$ for the Y-direction scanning electromagnet (=current value, current value calculated and corrected in consideration of hysteresis, set magnetic field intensity, etc.)

Kinetic Energy Command Value $E_b$ for Accelerator

The charged particle beam 1 which is irradiated upon reception of the command values passes through the first and second beam profile monitors 12 and 13, and the measured passage position coordinates ($x_a$, $y_a$), ($x_b$, $y_b$) are output from the first and second beam profile monitors 12 and 13. It is also assumed that the depth-direction coordinate z which the irradiated charged particle beam 1 reaches is uniquely determined on the basis of the kinetic energy of the charged particle. Data processing means 17 (FIG. 3) calculates the irradiation position coordinate (x,y,z) from these values ($x_a$, $y_a$), ($x_b$, $y_b$) and z.

As described above, the test irradiation for calibration is executed by fluctuating the respective command values. For example, the command value $I_a$ for the X-direction scanning electromagnet is fluctuated to $I_a + \Delta I_a, \ldots$, and the command value $I_b$ for the Y-direction scanning electromagnet is fluctuated to $I_b + \Delta I_b, \ldots$. Here, an example of a method of determining the coefficients (unknown parameters) of an inverse mapping from the actual data of the test irradiation will be described. The polynomial expression model shown in the mathematical expression 1 can be represented by using a matrix and vectors.

[mathematical expression 2]

$$\underset{Ac}{\underline{[1 \ x \ x^2 \ y \ xy \ y^2]}} \underset{Xc}{\begin{bmatrix} a_{00} & b_{00} \\ a_{01} & b_{01} \\ a_{02} & b_{02} \\ a_{10} & b_{10} \\ a_{11} & b_{11} \\ a_{20} & b_{20} \end{bmatrix}} = \underset{Be}{\underline{[I_{ae} \ I_{be}]}}$$

(mathematical expression 2)

Here, the matrix Ac is an input matrix of the inverse mapping including the irradiation position coordinates, a matrix Xc represents an unknown parameter matrix of the inverse mapping, and a matrix Be represents an output matrix of the inverse mapping including estimation values of the command values. The values of the unknown parameter matrix Xc have not yet been determined at this stage. The command values Bcarib for the test irradiation for calibration and the actual data of the irradiation positions Acarib are arranged according to the form of the mathematical expression 2 so as to form a vertically long matrix.

[mathematical expression 3]

$$\underset{Acarib}{\begin{bmatrix} 1 & x_0 & x_0^2 & y_0 & x_0 y_0 & y_0^2 \\ 1 & x_1 & x_1^2 & y_1 & x_1 y_1 & y_1^2 \\ \vdots & \vdots & \vdots & \vdots & \vdots & \vdots \\ 1 & x_n & x_n^2 & y_n & x_n y_n & y_n^2 \end{bmatrix}} \underset{Xc}{\begin{bmatrix} a_{00} & b_{00} \\ a_{01} & b_{01} \\ a_{02} & b_{02} \\ a_{10} & b_{10} \\ a_{11} & b_{11} \\ a_{20} & b_{20} \end{bmatrix}} = \underset{Bcarib}{\begin{bmatrix} I_{a0} & I_{b0} \\ I_{a1} & I_{b1} \\ \vdots & \vdots \\ I_{a_n} & I_{b_n} \end{bmatrix}}$$

(mathematical expression 3)

Here, the subscript numeral means the test irradiation number for calibration (in the above example, it means that test irradiation for n places is executed). The unknown parameter matrix Xc of the inverse mapping is determined according to the following expression based on the least square method.

[mathematical expression 4]

$$Xc = (A_{carib}^T A_{carib})^{-1} A_{carib}^T B_{carib}$$ (mathematical expression 4)

Here, the superscript T represents a transposed matrix.

After the respective coefficients of the polynomial expression are determined through the above calibration, the actual irradiation is executed. First, it is checked by the beam monitor (not shown) provided to the beam transport duct 1 whether the beam incident point to the scanning electromagnet 3a does not vary from that under the calibration. At this time, when it is found that the beam incident point varies, the calibration procedure may be executed again to determine the respective coefficients.

The order of the polynomial expression model of the mathematical expression 1, etc. may be properly increased in accordance with the characteristic of the particle beam irradiation apparatus being handled when it has strong non-linearity, and the order is not limited to the order=2 indicated in the mathematical expression 1. Some polynomial expression models (inverse mapping mathematical expression models) may be prepared in advance so that an operator can select any polynomial expression model. Furthermore, the method disclosed in the patent document 3 or the like calculates the correction amount, however, it is different from the present invention that the inverse map mathematical expression of this invention determines an command itself.

Figure 6:
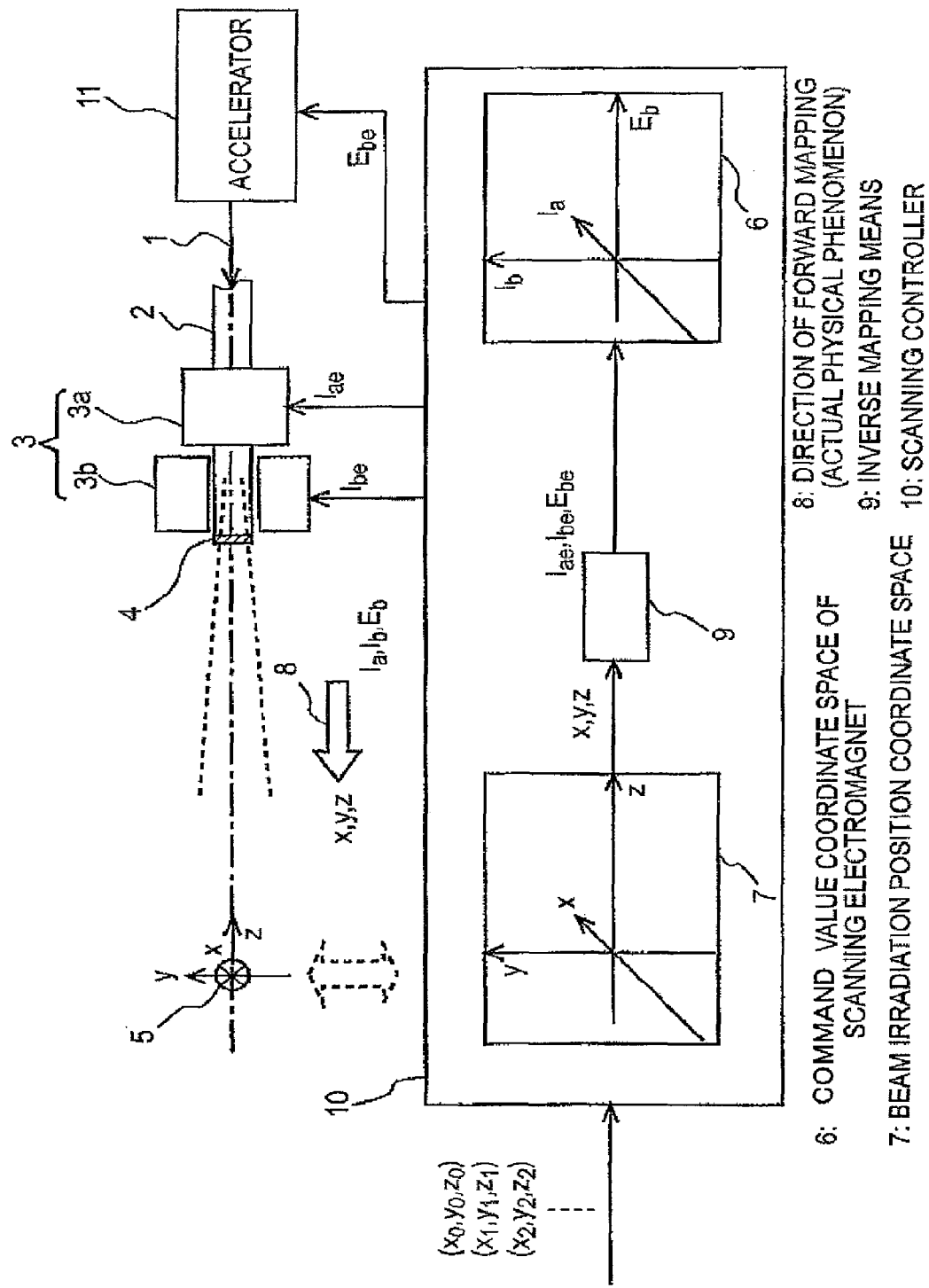
FIG. 6 is a diagram showing the construction of a particle beam irradiation apparatus according to a first embodiment of the present invention.

The particle beam irradiation apparatus is required to irradiate a charged particle beam three-dimensionally, and the desired beam irradiation position coordinate (x,y,z) is generally transmitted to the scanning controller 10 in the form of $(x_0, y_0, z_0)$ $(x_1, y_1, z_1)$ $(x_2, y_2, z_2)$, . . . as shown in FIG. 6.

Figure 5:
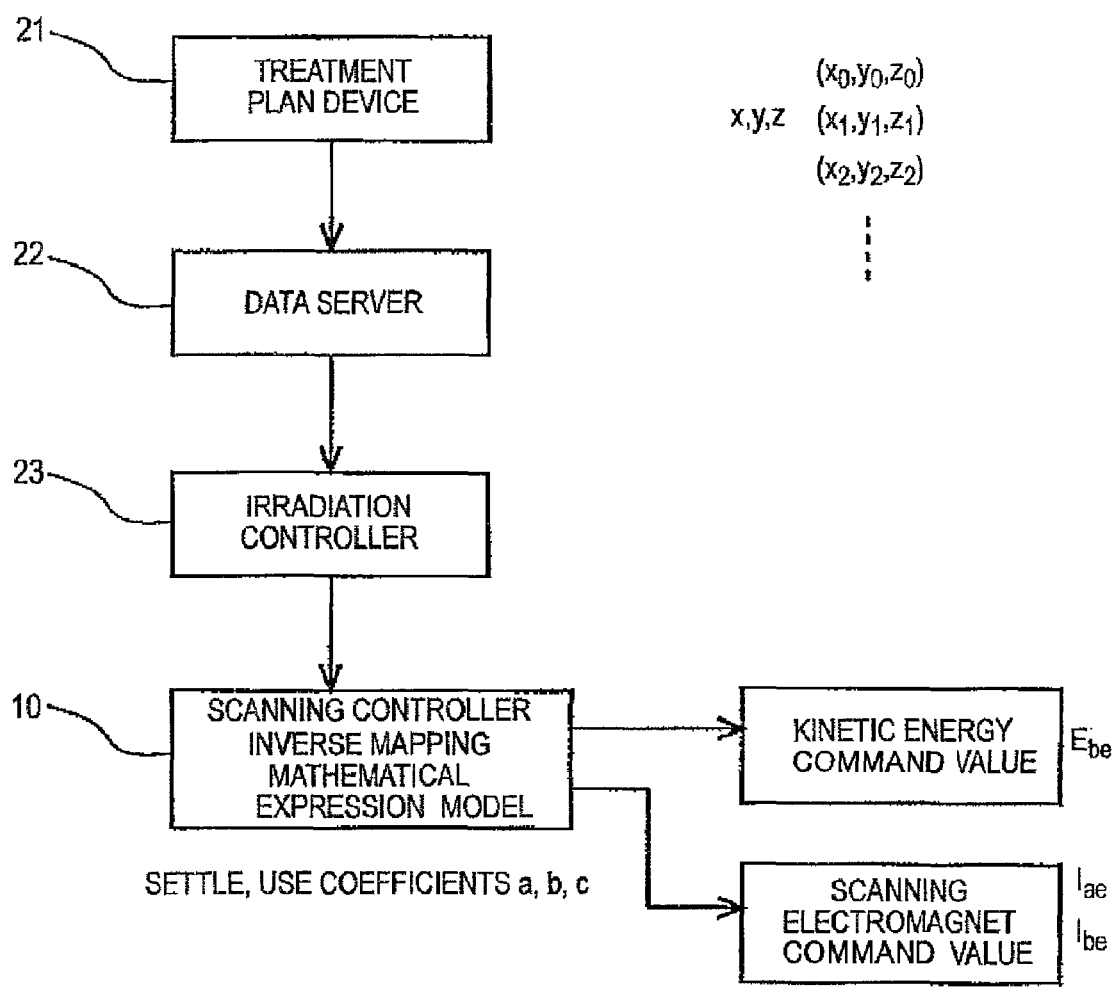
FIG. 5 is a block diagram for determining an command value for a scanning electromagnet and an command value for kinetic energy of a charged particle beam from a treatment plan value in the present invention.

FIG. 5 is a block diagram to determine the command values for the scanning electromagnets and the command value for the kinetic energy of the charged particle beam on the basis of treatment plan values. The desired beam irradiation position coordinates $(x_0, y_0, z_0)$ $(x_1, y_1, z_1)$ $(x_2, y_2, Z_2)$, . . . are transmitted through a data server 22 and the irradiation control device 23 to the scanning controller 10 by a treatment plan device 21 for a patient. The inverse mapping mathematical expression model and the kinetic energy command value $E_{be}$ in FIG. 5 will be described with reference to a first embodiment. As described above, the basic technique does not contain the control in the Z direction of the beam irradiation position with the kinetic energy of the charged particle beam of the accelerator set as a set value. Accordingly, when the beam incident point to the scanning electromagnet 3a is set not to vary, the desired beam irradiation position coordinates $(x_0, y_0)$ $(x_1, y_1)$ $(x_2, y_2)$, . . . are substituted into the inverse mapping mathematical expression model (mathematical expression 1) of the scanning controller 10, and the estimation values $(I_{ae}, I_{be})$, . . . of the scanning electromagnet command values are calculated for the respective desired beam irradiation position coordinates.

In the basic technique, the inverse mapping is determined for each of the plural different charged particle beam kinetic energies. Specifically, there are prepared not only the inverse mapping mathematical expression model for the mapping to a plane $A_0$-$A_0$ containing the isocenter 5 as the irradiation reference, but also inverse mapping mathematical expression models for mappings to planes $A_{-1}$-$A_{-1}$, $A_{-2}$-$A_{-2}$, . . . which are fixed in front of the isocenter 5 by changing the kinetic energy of the charged particle beam every $-\Delta E_b$ (it is unnecessary to fluctuate at even intervals) and inverse mapping mathematical expression models for mappings to $A_1$-$A_1$, $A_2$-$A_2$, . . . which are fixed at the backside of the isocenter 5 by changing the kinetic energy of the charged particle beam every $+\Delta E_b$. When the beam irradiation position coordinate in the irradiation subject is located between planes, linear interpolation is executed.

As described above, the basic technique is provided with the calculating means (inverse mapping means) for calculating estimation values $(I_{ae}, I_{be})$ of the command values for the scanning electromagnets with respect to the desired irradiation position coordinate (x,y) on the irradiation reference plane so that the irradiation at the desired irradiation position coordinate (x,y) on the irradiation reference plane is implemented. Specifically, the inverse mapping means has a polynomial expression model of 2-input and 2-output. Therefore, there can be obtained the high-precision and high-reliability particle beam irradiation apparatus which compensates the beam position precision in accordance with the individual difference of the particle beam irradiation apparatus as a target, use environment and secular variation.

First Embodiment

FIG. 6 is a diagram showing the construction of a particle beam irradiation apparatus according to a first embodiment. In the basic technique of the present invention, the inverse mapping mathematical expression model is treated as a 2-input 2-output model. However, in the first embodiment, the inverse mapping mathematical expression model is treated as a 3-input 3-output comprising desired irradiation position coordinates as shown in FIG. 6 and the following mathematical expression 5 (described later). The following mathematical expression 5 represents a polynomial expression model in the case of 3-input, 3-output and the maximum order=2.

[mathematical expression 5]

$$\begin{cases} I_{ae} = a_{000} + a_{001}x + a_{002}x^2 + a_{010}y + a_{011}xy + a_{020}y^2 + \\ \qquad a_{100}z + a_{101}xz + a_{110}yz + a_{200}z^2 \\ I_{be} = b_{000} + b_{001}x + b_{002}x^2 + b_{010}y + b_{011}xy + b_{020}y^2 + \\ \qquad b_{100}z + b_{101}xz + b_{110}yz + b_{200}z^2 \\ E_{be} = c_{000} + c_{001}x + c_{002}x^2 + c_{010}y + c_{011}xy + c_{020}y^2 + \\ \qquad c_{100}z + c_{101}xz + c_{110}yz + c_{200}z^2 \end{cases} \quad \text{(mathematical expression 5)}$$

Here, $a_{000}, a_{001}, a_{002}, \ldots, b_{000}, b_{001}, b_{002}, \ldots, c_{000}, c_{001}, c_{002}, \ldots$ represent coefficients (unknown parameters) for determining the characteristic of the inverse mapping mathematical expression model. $I_{ae}, I_{be}, E_{be}$ are estimation values of the X-direction and Y-direction command values for the X, Y-direction scanning electromagnets and an estimation value of an command value of kinetic energy of a charged particle beam for the accelerator when the irradiation position coordinate of the charged particle beam is $(x,y,z)$. That is, the X-direction, Y-direction and kinetic energy inverse mapping mathematical expression model (mathematical expression 5) for generating the X-direction command value $I_{ae}$, the Y-direction command value $I_{be}$ and the kinetic energy command value $E_{be}$ contains all three variables $(x,y,z)$ when the desired irradiation position coordinate is represented by the three variables $(x,y,z)$. The coefficients (unknown parameters) for determining the characteristic of the inverse mapping mathematical expression model are determined by performing test irradiation for calibration in advance and applying the least square method on the actual data of the test irradiation or the like as in the case of the basic technique of the present invention.

The test irradiation for calibration is executed by fluctuating the following values with the scanning controller 10.

Command value $I_a$ for the X-direction scanning electromagnet (=current value, current value calculated and corrected in consideration of hysteresis, set magnetic field intensity, etc.)

Command value $I_b$ for the Y-direction scanning electromagnet (=current value, current value calculated and corrected in consideration of hysteresis, set magnetic field intensity, etc.)

Kinetic Energy Command Value $E_b$ for Accelerator

Upon reception of the command values, the irradiated charged particle beam 1 passes through the first and second beam profile monitors 12, 13, and measured passage position coordinates $(x_a, y_a)$, $(x_b, y_b)$ are output from the first and second beam profile monitors 12 and 13 as shown in FIGS. 2, 3 and 4. Furthermore, the irradiated charged particle beam 1 arrives at the water phantom 14, and the coordinate $z_p$ in the depth direction of the position coordinate at which it arrives is output. The data processing means 17 (FIG. 3) which obtains these output values determines $(x_p, y_p)$ of the arrival position coordinate from $(x_a, y_a)$, $(x_b, y_b)$ and $Z_p$, and determines the arrival position coordinate $(x_p, y_p, z_p)$.

As described above, the test irradiation for calibration is executed by fluctuating the value of each command value. For example, the command value $I_a$ for the X-direction scanning electromagnet is fluctuated to $I_a + \Delta I_a, \ldots$, the command value $I_b$ for the Y-direction scanning electromagnet is fluctuated to $I_b + \Delta I_b, \ldots$, and the kinetic energy command value $E_b$ for the accelerator is fluctuated to $E_b + \Delta E_b, \ldots$. Here, an example of a method of determining the coefficients (unknown parameters) of the inverse mapping in the case of 3-input and 3-output from the actual data of the test irradiation will be described. The polynomial expression model shown in the mathematical expression 5 can be represented as follows by using a matrix and vectors.

[mathematical expression 6]

$$\underbrace{\begin{bmatrix} 1 & x & x^2 & y & xy & y^2 & z & xz & yz & z^2 \end{bmatrix}}_{Ac} \underbrace{\begin{bmatrix} a_{000} & b_{000} & a_{000} \\ a_{001} & b_{001} & c_{001} \\ a_{002} & b_{002} & c_{002} \\ a_{010} & b_{010} & c_{010} \\ a_{011} & b_{011} & c_{011} \\ a_{020} & b_{020} & c_{020} \\ a_{100} & b_{100} & c_{100} \\ a_{101} & b_{101} & c_{101} \\ a_{110} & b_{110} & c_{110} \\ a_{200} & b_{200} & c_{200} \end{bmatrix}}_{Xc} = \underbrace{\begin{bmatrix} I_{ae} & I_{be} & E_{be} \end{bmatrix}}_{Be} \quad \text{(mathematical expression 6)}$$

Here, the matrix Ac represents an input matrix of the inverse mapping comprising the irradiation position coordinates, the matrix Xc represents an unknown parameter matrix of the inverse mapping, and the matrix Be represents an output matrix of the inverse mapping comprising estimation values of command values. The values of the unknown parameter matrix Xc have not yet been determined at this stage. The command values obtained in the test irradiation for calibration and the actual data of the irradiation positions are arranged according to the form of the mathematical expression 6 so as to form a vertically long matrix. The command values Bcarib in the case of the test irradiation for calibration and the actual data of the obtained irradiation positions Acarib are arranged vertically according to the form of the mathematical expression 6 so as to form a vertically long matrix.

[mathematical expression 7]

(mathematical expression 7)

$$\underset{Acarib}{\begin{bmatrix} 1 & x_0 & x_0^2 & y_0 & x_0 y_0 & y_0^2 & z_0 & x_0 z_0 & y_0 z_0 & z_0^2 \\ 1 & x_1 & x_1^2 & y_1 & x_1 y_1 & y_1^2 & z_1 & x_1 z_1 & y_1 z_1 & z_1^2 \\ \vdots & \vdots & \vdots & \vdots & \vdots & \vdots & \vdots & \vdots & \vdots & \vdots \\ 1 & x_n & x_n^2 & y_n & x_n y_n & y_n^2 & z_n & x_n z_n & y_n z_n & z_n^2 \end{bmatrix}}$$

$$\underset{Xc}{\begin{bmatrix} a_{000} & b_{000} & c_{000} \\ a_{001} & b_{001} & c_{001} \\ a_{002} & b_{002} & c_{002} \\ a_{010} & b_{010} & c_{010} \\ a_{011} & b_{011} & c_{011} \\ a_{020} & b_{020} & c_{020} \\ a_{100} & b_{100} & c_{100} \\ a_{101} & b_{101} & c_{101} \\ a_{110} & b_{110} & c_{110} \\ a_{200} & b_{200} & c_{200} \end{bmatrix}} = \underset{Bcarib}{\begin{bmatrix} I_{a0} & I_{b0} & E_{b0} \\ I_{a1} & I_{b1} & E_{b1} \\ \vdots & \vdots & \vdots \\ I_{a_n} & I_{b_n} & E_{b_n} \end{bmatrix}}$$

Here, the subscript numeral means the test irradiation number of calibration (in the above example, it means that the test irradiation for n places is executed). The unknown parameter matrix Xc of the inverse mapping is determined by the mathematical expression 4 based on the least square method as in the case of the basic technique. After the respective coefficients of the polynomial expression is determined by the above calibration, the actual irradiation is executed. First, it is checked by the beam monitor (not shown) provided to the beam transport duct 1 that the beam incident point to the scanning electromagnet 3a does not vary from that at the calibration time. At this time, when it is found that the beam incident point varies, the calibration procedure may be executed again to determine the respective coefficients.

The order of the polynomial expression model as the inverse mapping mathematical expression mode may be properly increased in accordance with the characteristic of the particle beam irradiation apparatus being handled when it has strong non-linearity, and the order is not limited to the order=2 indicated in the mathematical expression 5. In the first embodiment, some polynomial expression models may be also prepared in advance so that an operator can select any polynomial expression model.

In the first embodiment, the desired beam irradiation position coordinates $(x_0, y_0, z_0)$ $(x_1, y_1, z_1)$ $(x_2, y_2, z_2)$ . . . are also transmitted through the data server 22 and the irradiation control device 23 to the scanning controller 10 by the treatment plan device 21 for a patient as shown in FIG. 5. When the beam incident point to the scanning electromagnet 3a is set not to vary, the transmitted desired beam irradiation position coordinates $(x_0, y_0, z_0)$ $(x_1, y_1, z_1)$ $(x_2, y_2, z_2)$ . . . are substituted into the inverse mapping mathematical expression model (mathematical expression 5) of the scanning controller 10, and the estimation values $(I_{ae}, I_{be})$ . . . of the command values for the scanning electromagnets and the estimation values $(E_{be})$ . . . of the kinetic energy command values are calculated for the respective desired beam irradiation position coordinates.

The position control of the charged particle beam is roughly performed by the scanning electromagnet 3 for the X and Y directions and by the adjustment of the kinetic energy of the charged particle beam for the Z direction. However, strictly, the control cannot be so clearly divided into XY and Z. When the charged particle beam is controlled by the scanning electromagnet 3, it affects not only the XY directions, but also the Z direction. Likewise, when the kinetic energy of the charged particle beam is controlled, not only the Z direction, but also the XY directions may be affected. Such an effect as described above is referred to as "interference term effect between XY and Z. The inverse mapping mathematical expression model of 3-input and 3-output can generate the command values in consideration of the interference term effect between XY and Z.

In the conventional methods based on deflection correction (for example, patent document 3), no attention is paid to the Z direction. However, according to the first embodiment, the Z-direction is also considered by preparing plural inverse mapping mathematical expression models as described above.

As described above, the inverse mapping mathematical model in the scanning controller 10 is set to the 3-input and 3-output comprising the desired irradiation position coordinates. Therefore, the command values for the scanning electromagnet 3 and the kinetic energy command value for the charged particle beam 1 can be determined at a time, and the command values can be generated in consideration of the interference term effect between XY and Z, so that the beam position control can be implemented with higher precision. Furthermore, there can be implemented a high-precision beam irradiation position which is dependent on the fan beam effect and the cone beam effect and considers the variation of the irradiation position coordinate. Still furthermore, a conversion table may be prepared as an inverse mapping model for generating an command value for the scanning electromagnet and an command value for the kinetic energy of the charged particle beam from a desired irradiation position coordinate of the charged particle beam in the irradiation subject so that the irradiation to the desired irradiation position coordinate is implemented, and the scanning electromagnet and the kinetic energy of the charged particle beam may be controlled on the basis of the command values generated from the desired irradiation position coordinate of the charged particle beam in the irradiation subject by using the conversion table, thereby irradiating the irradiation subject with the charged particle beam while scanning the charged particle beam.

Second Embodiment

Figure 7:
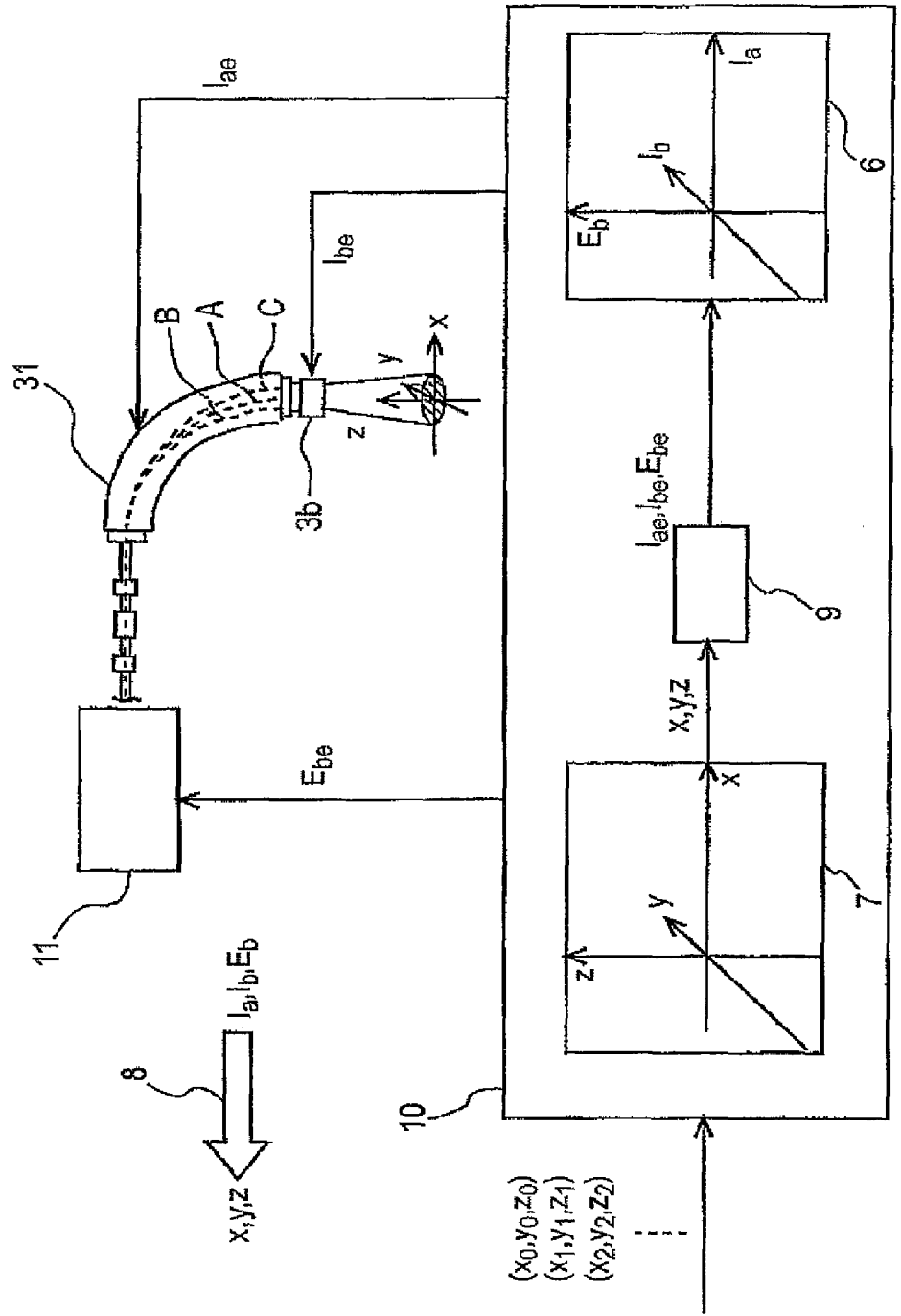
FIG. 7 is a diagram showing the construction of a particle beam irradiation apparatus according to a second embodiment of the present invention.

FIG. 7 is a diagram showing the construction of a particle beam irradiation apparatus according to a second embodiment. 31 represents a final bending electromagnet provided to the beam transport system, and it is disposed upstream of the Y-direct ion scanning electromagnet 3b and deflects the charged particle beam to A, B and C passages. FIG. 1 of the basic technique of the invention shows a simple case where the scanning electromagnet 3 is disposed at the most downstream side. However, there is a case where the bending electromagnet is disposed at the downstream side of the scanning electromagnet (scanning electromagnet, wobbler electromagnet) as in the case of the particle beam irradiation apparatus of the patent document 1, or a case where the scanning electromagnet is omitted by making good use of the bending electromagnet as in the case of the particle beam irradiation apparatus of the patent document 2. This invention can be applied to the above constructions. In these cases, the forward mapping from the command value coordinate space 6 to the beam irradiation position coordinate space 7 is more complicated, and thus the effect of this invention is greater.

In FIG. 7, the Y-direction scanning electromagnet 3b is used, and the final bending electromagnet 31 is brought with the function of the X-direction scanning electromagnet. The command value $I_a$ for the X-direction scanning electromagnet is generated from the final bending electromagnet 31, the charged particle beam is scanned, and the estimation value $I_{ae}$ of the command value for the X-direction scanning electromagnet is input to the final bending electromagnet 31. As described above, the final bending electromagnet 31 is brought with the same function as the X-direction scanning electromagnet.

Third Embodiment

In the first embodiment, the least square method is described as the method of determining the coefficients (unknown parameters) of the polynomial expression. When the coefficients (unknown parameters) of the polynomial expression are determined, a weighted least square method may be used. According to the weighted least square method, the calculation is performed while respective original data (actual data at the calibration time) for determining the coefficients (unknown parameters) of the polynomial expression are weighted. For example, there is a case where low-reliability data are obtained due to some factor (for example, electrical noise or the like) in the test irradiation for calibration. In this case, the low-reliability data are multiplied by a weight which is near to zero, whereby the influence of these data can be suppressed.

Furthermore, the irradiation subject may be divided into some areas, and the unknown parameters of the polynomial expression may be determined every area. In this case, when the polynomial expression of some area A is calculated, the calculation is performed while data belonging to the area A are multiplied by a weight "1" and data which do not belong to the area A is multiplied by a weight near to zero, whereby irradiation nearer to an actual phenomenon, that is, high-precision irradiation can be implemented.

What is claimed is:

1. A particle beam irradiation apparatus comprising:
an accelerator;
a scanning electromagnet; and
a controller for controlling the accelerator and the scanning electromagnet to irradiate a charged particle beam from the accelerator to an irradiation subject,
the scanning electromagnet having: an X-direction scanning electromagnet; and
a Y-direction scanning electromagnet for scanning in a direction perpendicular to a scanning direction of the X-direction scanning electromagnet,
the controller having: an X-direction inverse mapping mathematical expression model for generating an X-direction command value for exciting the X-direction scanning electromagnet;
a Y-direction inverse mapping mathematical expression model for generating a Y-direction command value for exciting the Y-direction scanning electromagnet; and
a kinetic energy inverse mapping mathematical expression model for generating a command value of kinetic energy for the accelerator for accelerating the charged particle beam,
from a desired irradiation position coordinate of the charged particle beam in the irradiation subject so that irradiation to the irradiation subject is implemented on the basis of the command values concerned,
each of the X-direction, Y-direction and kinetic energy inverse mapping mathematical expression models containing all of three variables when the desired irradiation position coordinate is represented by the three variables concerned,
wherein the X-direction and Y-direction scanning electromagnets and the accelerator are controlled on the basis of the X-direction, Y-direction and kinetic energy command values generated from the desired irradiation position coordinate of the charged particle beam in the irradiation subject by the X-direction, Y-direction and kinetic energy inverse mapping mathematical expression models to control the charged particle beam, thereby irradiating the irradiation subject with the charged particle beam.

2. The particle beam irradiation apparatus according to claim 1, wherein each of the X-direction, Y-direction and kinetic energy inverse mapping mathematical expression models is a polynomial expression.

3. The particle beam irradiation apparatus according to claim 2, wherein unknown coefficients existing in each of the X-direction, Y-direction and kinetic energy inverse mapping mathematical expression models as the polynomial expressions are determined by inputting plural pairs of command values preset for the X-direction and Y-direction scanning electromagnets and also inputting plural preset kinetic energy command values to the accelerator to control the charged particle beam, and applying a least square method or a weighted least square method to actual data of actually irradiated irradiation position coordinates.

4. The particle beam irradiation apparatus according to claim 1, wherein plural sets of the X-direction, Y-direction and kinetic energy inverse mapping mathematical expression models are provided, and the X-direction, Y-direction and kinetic energy inverse mapping mathematical expression models to be used can be selected from the plural sets of inverse mapping mathematical expression models.

5. The particle beam irradiation apparatus according to claim 1, wherein a bending electromagnet provided to a beam transport system is brought with a function of the X-direction or Y-direction scanning electromagnet.

6. A particle beam irradiation apparatus comprising:
an accelerator;
a scanning electromagnet; and
a controller for controlling the accelerator and the scanning electromagnet to irradiate a charged particle beam from the accelerator to an irradiation subject,
the scanning electromagnet having: an X-direction scanning electromagnet; and
a Y-direction scanning electromagnet for scanning in a direction perpendicular to a scanning direction of the X-direction scanning electromagnet,
the controller having: an X-direction inverse mapping mathematical expression model for generating an X-direction command value for exciting the X-direction scanning electromagnet; and
a Y-direction inverse mapping mathematical expression model for generating a Y-direction command value for exciting the Y-direction scanning electromagnet,
from a desired irradiation position coordinate of the charged particle beam in the irradiation subject so that irradiation to the irradiation subject is implemented on the basis of the command values concerned, the X-direction and Y-direction inverse mapping mathematical expression models being polynomial expressions containing variables representing the desired irradiation position coordinate, wherein unknown coefficients contained in the polynomial expressions are determined by inputting a plurality of pairs of preset X-direction and Y-direction command values to the X-direction and Y-direction scanning electromagnets and also inputting a plurality of preset kinetic energy command values to the accelerator to control a charged particle beam and performing a weighting least-square method of executing lower weighting on some data of actual data of irradiation position coordinates at which the charged particle beam is actually irradiated, thereby enhancing reliability.

7. The particle beam irradiation apparatus according to claim 6, wherein the controller has: the X-direction inverse mapping mathematical expression model for generating an X-direction command value for exciting the X-direction scanning electromagnet;

the Y-direction inverse mapping mathematical expression model for generating a Y-direction command value for exciting the Y-direction scanning electromagnet; and a kinetic energy inverse mapping mathematical expression model for generating a command value of kinetic energy for the accelerator for accelerating the charged particle beam, from a desired irradiation position coordinate of the charged particle beam in the irradiation subject so that irradiation to the irradiation subject is implemented on the basis of the command values concerned, the X-direction, Y-direction and kinetic energy inverse mapping mathematical expression models are polynomial expressions containing variables representing the desired irradiation position coordinate, and unknown coefficients contained in the polynomial expressions are determined by inputting a plurality of pairs of preset X-direction and Y-direction command values to the X-direction and Y-direction scanning electromagnets and also inputting a plurality of preset kinetic energy command values to the accelerator to control a charged particle beam and performing a weighting least-square method of executing lower weighting on some data of actual data of irradiation position coordinates at which the charged particle beam is actually irradiated, thereby enhancing reliability.

8. A particle beam irradiation apparatus comprising:
an accelerator;
a scanning electromagnet; and
a controller for controlling the accelerator and the scanning electromagnet to irradiate a charged particle beam from the accelerator to an irradiation subject,
the scanning electromagnet having: an X-direction scanning electromagnet; and
a Y-direction scanning electromagnet for scanning in a direction perpendicular to a scanning direction of the X-direction scanning electromagnet,
the controller having: an X-direction inverse mapping mathematical expression model for generating an X-direction command value for exciting the X-direction scanning electromagnet; and a Y-direction inverse mapping mathematical expression model for generating a Y-direction command value for exciting the Y-direction scanning electromagnet, from a desired irradiation position coordinate of the charged particle beam in the irradiation subject so that irradiation to the irradiation subject is implemented on the basis of the command values concerned, the X-direction and Y-direction inverse mapping mathematical expression models being polynomial expressions containing variables representing the desired irradiation position coordinate, wherein in order to determine unknown coefficients contained in the polynomial expressions, the irradiation subject is divided into plural areas, and the unknown coefficients contained in the polynomial expressions of each area are determined by inputting a plurality of pairs of preset X-direction and Y-direction command values to the X-direction and Y-direction scanning electromagnets and also inputting a plurality of preset kinetic energy command values to the accelerator to control a charged particle beam, and subjecting actual data of each actually-irradiated irradiation position coordinate to a weighting least-square method of executing weighting such that a weight of actual data belonging to the area concerned is larger than a weight of actual data which do not belong to the area concerned.

9. The particle beam irradiation apparatus according to claim 8, wherein the controller has: the X-direction inverse mapping mathematical expression model for generating an X-direction command value for exciting the X-direction scanning electromagnet;

the Y-direction inverse mapping mathematical expression model for generating a Y-direction command value for exciting the Y-direction scanning electromagnet; and a kinetic energy inverse mapping mathematical expression model for generating an command value of kinetic energy for the accelerator for accelerating the charged particle beam, from a desired irradiation position coordinate of the charged particle beam in the irradiation subject so that irradiation to the irradiation subject is implemented on the basis of the command values concerned, the X-direction, Y-direction and kinetic energy inverse mapping mathematical expression models are polynomial expressions containing variables representing the desired irradiation position coordinate, and in order to determine unknown coefficients contained in the polynomial expression, the irradiation subject is divided into plural areas, and the unknown coefficients contained in the polynomial expression of each area are determined by inputting a plurality of pairs of preset X-direction and Y-direction command values to the X-direction and Y-direction scanning electromagnets and also inputting a plurality of preset kinetic energy command values to the accelerator to control a charged particle beam, and subjecting actual data of each actually-irradiated irradiation position coordinate to a weighting least-square method of executing weighting such that a weight of actual data belonging to the area concerned is larger than a weight of actual data which do not belong to the area concerned.

* * * * *